(12) United States Patent
Hillier et al.

(10) Patent No.: US 7,306,596 B2
(45) Date of Patent: Dec. 11, 2007

(54) MULTIFUNCTIONAL ELECTROSURGICAL APPARATUS

(75) Inventors: Taylor Hillier, Etobicoke (CA); Krishan Shah, Mississauga (CA); Laura Conquergood, Mississauga (CA); Neil Godara, Mississauga (CA); Abraham Roza, Burlington (CA)

(73) Assignee: Baylis Medical Company Inc., Mississauga, Ontario (CA)

( * ) Notice: Subject to any disclaimer, the term of this patent is extended or adjusted under 35 U.S.C. 154(b) by 127 days.

(21) Appl. No.: 11/125,247

(22) Filed: May 10, 2005

(65) Prior Publication Data

US 2005/0267465 A1 Dec. 1, 2005

Related U.S. Application Data

(63) Continuation-in-part of application No. 10/853,126, filed on May 26, 2004.

(51) Int. Cl.
*A61B 18/18* (2006.01)
(52) U.S. Cl. .................... 606/41; 128/898; 606/34
(58) Field of Classification Search ........... 606/32–52; 128/898
See application file for complete search history.

(56) References Cited

U.S. PATENT DOCUMENTS

| 4,311,145 | A | | 1/1982 | Esty et al. |
|---|---|---|---|---|
| 4,411,266 | A | | 10/1983 | Cosman |
| 5,275,597 | A | * | 1/1994 | Higgins et al. ............. 606/33 |
| 5,281,218 | A | | 1/1994 | Imran |
| 5,342,357 | A | | 8/1994 | Nardella |
| 5,433,739 | A | | 7/1995 | Sluijter et al. |
| 5,605,539 | A | | 2/1997 | Buelna et al. |
| 5,725,524 | A | | 3/1998 | Mulier |
| 5,824,007 | A | | 10/1998 | Faraz et al. |
| 5,893,885 | A | | 4/1999 | Webster, Jr. et al. |
| 5,951,546 | A | | 9/1999 | Lorentzen |
| 5,957,922 | A | | 9/1999 | Imran |
| 6,063,080 | A | | 5/2000 | Nelson et al. |
| 6,123,703 | A | * | 9/2000 | Tu et al. ..................... 606/41 |
| 6,146,380 | A | | 11/2000 | Racz et al. |
| 6,238,393 | B1 | * | 5/2001 | Mulier et al. ............... 606/41 |
| 6,283,961 | B1 | | 9/2001 | Underwood et al. |

(Continued)

OTHER PUBLICATIONS

J. Geurts, R. Wijk, R. Stolker, G.Groen. "Efficacy of radiofrequency procedures for the treatment of spinal pain: A systemic review of randomized clinical trials". Regional Anesthesia and Pain Medicine. Sep.-Oct. 26, 2001(5):394-400.

(Continued)

*Primary Examiner*—Henry M Johnson, III
(74) *Attorney, Agent, or Firm*—Dimock Stratton LLP; Mark B. Eisen

(57) ABSTRACT

An electrosurgical apparatus having improved placement accuracy is provided. The electrosurgical apparatus comprises an elongate shaft having a proximal end, a distal end and at least one lumen therethrough, a stylet positioned within a lumen, a conductive tip at the distal end for delivery of energy to the tissue, an electrical coupling at or near the proximal end for flexibly coupling a power source control unit to supply energy to the conductive tip, a fluid delivery connection interface flexibly coupled at or near the proximal end for coupling a fluid delivery mechanism. The apparatus further comprises a temperature sensor. A method of delivering electrical energy to a target treatment area of an animal body is also provided.

25 Claims, 12 Drawing Sheets

U.S. PATENT DOCUMENTS

| | | | |
|---|---|---|---|
| 6,315,777 B1* | 11/2001 | Comben | 606/41 |
| 6,463,332 B1 | 10/2002 | Aldrich | |
| 6,464,661 B2 | 10/2002 | Edwards et al. | |
| 6,547,788 B1* | 4/2003 | Maguire et al. | 606/41 |
| 6,730,079 B2* | 5/2004 | Lovewell | 606/34 |
| 2003/0088243 A1 | 5/2003 | Carmel et al. | |
| 2003/0158545 A1 | 8/2003 | Hovda et al. | |
| 2003/0208250 A1 | 11/2003 | Edwards et al. | |
| 2004/0015164 A1 | 1/2004 | Fuimaono et al. | |
| 2004/0019350 A1 | 1/2004 | O'Brien et al. | |
| 2004/0024399 A1* | 2/2004 | Sharps et al. | 606/41 |
| 2005/0107781 A1* | 5/2005 | Ostrovsky et al. | 606/41 |

OTHER PUBLICATIONS

R. Leclaire, L. Fortin, R. Lambert, Y.M. Bergeron, M. Rossignol. "Radiofrequency Facet Joint Denervation in the Treatment of Low Back Pain: A Placebo Controlled Clinical Trial to Assess Efficacy". Spine. Mar. 1, 2002;27(5):556-7.

"Disposable RF Cannulae and RF Electrodes: RF Pole Needles". Radionics Sales Brochure. 1997.

"Neurotherm Disposable Stimject Kit". RDG Medical Sales Brochure. 2003.

"Neurotherm Disposable RF electrode". RDG Medical Sales Brochure. 2003.

"510(k) for Radionics RF Pole Needles". Food and Drug Administration. Sep. 2002.

Douglas S. Fenton, Leo F. Czervionke. "Image Guided Spine Intervention". p. 63. 2003.

Dodd GD; Soulen MC; Kane RA; Livraghi T; Lees WR, Yamashita Y; Gillams AR; Karahan Ol; Rhim H. "Minimally Invasive Treatment of Malignant Hepatic Tumors: At the Threshold of a Major Breakthrough." Radiographics 2000; 20:9-27.

Dupuy DE; Zagoria RJ; Akerley W; Mayo-Smith WW; Kavanagh PV; Safran H. "Percutaneous Radiofrequency Ablation of Malignancies in the Lung." American Journal Roentgenol 174(1):57-9, Jan. 2000.

Goldberg S; Gazelle G; Sheiman R; Kruskal J; Clouse M. "Percutaneous Radiofrequency Tissue Ablation: Optimization of Pulsed-Radiofrequency Technique to Increase Coagulation Necrosis." JVIR 10:907-916, 1999.

Goldberg S; Gazelle G; Solbiati L; Rittman W; Mueller P. "Radiofrequency Tissue Ablation: Increased Lesion Diameter with a Perfusion Electrode." Acad Radiol 1996; 3:636-644, 1996.

Goldberg NS; Hahn PF; Halpern Ef; Fogle RM; Gazelle GS. "Radio-frequency Tissue Ablation: Effect of Pharmacologic Modulation of Blood Flow on Coagulation Diameter." Radiology 1998; 209:761-67.

Goldberg NS; Solbiati L; Hahn PF; Cosman E; Conrad JE; Fogle R; Gazelle Gs. Large-Volume Tissue Ablation with radio Frequency by Using a Clustered, Internally Cooled Electrode Technique: Laboratory and Clinical Experience in Liver Metastases.: Radiology 1998 209: 371-79.

Radionics Cool-Tip RF Ablation System Brochure 2001.

Goldberg NS; Gazelle GS; Dawson SI; Rittman WJ; Mueller PR; Rosenthal DI. "Tissue Ablation with radiofrequency Using Multiprobe Arrays." Academic Radiology 1995;2:670-74.

Solbiati L'Goldberg NS; Ierace T; Livraghi T; Meloni F; Dellanoce M; Sironi S; Gazelle GS. "Hepatic Metastases: Percutaneous Radio-Frequency Ablation with Cooled-Tip Electrodes." Radiology 205:367-373, Nov. 1997.

Livraghi T; Goldberg NS; Lazzaroni S; Meloni F; Solbiati L; Gazelle GS. "Small Hepatocellular Carcinoma: Treatment with Radio-frequency Ablation versus Ethanol Injection." Radiology 1999;210:655-61.

Rosenthal D; Springfield D; Gebhardt M; Rosenberg A; Mankin H. "Osteoid Osteoma: Percutaneous Radio-Frequency Ablation." Radiology 197 (2):451-454.

* cited by examiner

MULTIFUNCTIONAL ELECTROSURGICAL APPARATUS

CROSS-REFERENCE TO RELATED APPLICATION

This application is a continuation-in-part of U.S. application Ser. No. 10/853,126, filed May 26, 2004.

TECHNICAL FIELD

The present invention relates to electrosurgical devices and more particularly to devices used to deliver high or radio frequency electrical current to a target area in a body.

BACKGROUND OF THE INVENTION

Electrosurgical procedures typically rely on the application of high frequency, for example radio frequency (RF), energy to treat, cut, ablate or coagulate tissue structures such as, for example, neural tissue. One example of a treatment procedure incorporating the application of RF energy to treat neural tissue is lumbar facet denervation. The efficacy of the minimally invasive technique of delivering RF electrical current to neural tissue in lumbar facet denervation has been studied at length and these studies show that this procedure is an effective method of relieving low back pain. The high frequency energy is often delivered to a region of tissue from an energy source such as a generator via a probe that is inserted into a patient's body through an introducer needle. The resistance of tissue, located proximate a conductive region of the probe, to the high frequency energy, causes the tissue temperature to rise. The temperature is generally increased to a sufficient level to coagulate unmyelinated nerve structures, at which point a lesion is formed, resulting in pain relief. The probe is typically a stainless steel electrode that is manufactured to fit within an introducer needle (which may also be referred to as a cannula or tube). Some probes incorporate a temperature sensor to allow for monitoring of temperature throughout the procedure. The temperature can be used to control the delivery of the high frequency energy.

Introducer needles with varying geometries are used in such applications. For example, a tip of the introducer needle can be pointed, blunt and rounded, or open, varying in shape in accordance with the needs of different procedures. Pointed tips allow for penetration of tissue without the need for an external device while rounded tips are useful in soft tissue areas such as the brain where it is critical not to damage nerves. However, it should be noted that blunt introducer needles can do more tissue damage than small-diameter sharp introducer needles. U.S. Pat. No. 6,146,380 to Racz et al. describes introducer needles with curved conductive tips used in high frequency lesioning procedures. An introducer needle typically includes an insulated shaft with an electrically exposed and conductive tip at the distal end of the introducer. A hub at the proximal end of the introducer can also be provided as a connection site for an injection syringe. Introducer needles can therefore be used to inject anesthetic fluid or other treatment compositions, such as therapeutic agents, in addition to playing a role in the insertion of a device into a patient's body and the delivery of electrical energy to a region of tissue.

A typical treatment procedure utilizes an introducer needle having a hollow shaft and a removable stylet therein. This introducer needle is inserted into the patient's body and positioned via imaging technology. Once the introducer needle is positioned, the stylet is withdrawn. The distal end of the probe is then inserted into the shaft of the introducer needle until the distal end of the probe is at least flush with the distal end of the shaft. The probe is connected to a generator that generates electrical current. To ensure that only certain nerves will be treated, a stimulation procedure may be employed. This stimulation involves the delivery of low frequency electrical current in order to excite nerves. This procedure can differentiate between motor and sensory nerves and can confirm that the nerve to be treated is in fact the source of pain.

After placement is confirmed with the stimulation procedure, the probe is withdrawn. A syringe is then attached to the proximal end hub of the introducer needle in order to inject anesthetic fluid or other treatment compositions into the tissue. Following this injection of material, the syringe is removed and the probe is reinserted into the shaft of the introducer needle. Finally, high frequency electrical current is applied from the generator, via the probe and introducer needle, to the tissue adjacent the conductive tip and a lesion is formed. This high frequency electrical current generally returns to the generator through a return (also known as dispersive) electrode typically placed on an exterior surface of the patient's body.

Such a procedure can be used to denervate (that is, to neutralize the ability of neural tissue to convey signals to a patient's brain) specific portions of a patient's spine. Similar procedures may also be applied to other anatomical areas such as intercostal and trigeminal nerves. Accurate placement of the introducer needle's conductive tip in a complicated structure like the spine requires great technical skill by the treating physician. In these procedures, the introducer needle is often viewed via X-ray fluoroscopy, which assists in visualizing the introducer as it's guided into the patient's body.

One limitation of this technique is that placement achieved at the beginning of a procedure can be unintentionally altered by the attachment of a fluid delivery mechanism, for example a syringe, the actuation of the fluid delivery mechanism, or the removal and re-insertion of the probe after the stimulation procedure is complete. For example, to ensure that the fluid being injected does not leak, the fluid delivery mechanism must be tightly secured to the hub of the introducer needle. This twisting or pushing motion applies pressure to the introducer needle thus altering its placement within the body. Also, the probes are generally designed in such a manner that they are only slightly smaller than the inner diameter of the introducer needle to allow for a good electrical connection between the probe and the conductive tip region of the introducer needle. This tight fit requires the application of relatively high insertion forces to align the distal end of the probe with the end of the introducer needle. Therefore when the probe is inserted, removed or reinserted after the injection of a treatment composition, the forces applied can move the introducer needle. Movement caused by any of these inherent procedural complications creates a potential for unpredictable lesion development due to possible repositioning of the probes. The range of distance within which the tip of the introducer needle may move (thus altering the position of the probe) depends on the depth of the needle and the properties of the tissue. The tip may move radially up to 5 mm and axially up to 10 mm. Even slight variations in position can affect the outcome of the procedure. Therefore, placement often relies on the physician to visually monitor the position of the conductive tip throughout the procedure. However, variations in position can be so slight as to go unnoticed by a physician using the imaging technology currently available. Repeating the stimulation procedure to confirm the position of the probe following reinsertion is not viable since anesthetic has already been introduced. Thus, it would be beneficial to have a device or apparatus that would reduce or eliminate the need for those procedural steps that may result in unintentional movement of the introducer needle or probe.

Thus, based on the current state of the art, a need generally exists for an electrosurgical device or apparatus capable of overcoming some or all of the limitations and deficiencies of the prior art.

SUMMARY OF THE INVENTION

The present invention provides an electrosurgical apparatus with improved positioning characteristics. According to one broad aspect of the invention, an electrosurgical apparatus is provided for treating tissue. The apparatus comprises: an elongate shaft having a proximal region, a distal region, which comprises a conductive region, and one or more lumens therethrough; one or more apertures defined by the shaft and in communication with at least one lumen; a stylet occluding at least a portion of an opening defined by a distal end of the elongate shaft; an electrical coupling associated with the proximal region for flexibly coupling to a power source for supplying energy to the conductive region; a temperature sensor associated with the distal region; and at least one fluid delivery interface connection flexibly coupled to the proximal region for coupling a fluid delivery mechanism to deliver a treatment composition through at least one of the apertures.

In some embodiments of the invention, the temperature sensor is a thermocouple, and the thermocouple may include one or more of the conductive region and the stylet as its components. In certain embodiments, the stylet may be attached to the shaft of the apparatus. Some embodiments comprise one or more apertures located on a side of the shaft, with smooth walls for minimizing trauma to bodily tissue. Further possible features of the apparatus include one or more markers, including, for example, radiopaque markers and orientation markers. In addition, one or more of the shaft lumens may house wiring for connecting the conductive region to the energy source or for transmitting temperature measurements. Another possible feature that may be included in the apparatus is a handle associated with the proximal region of the shaft. The handle may include one or more markings, for example orientation markings, a strain relief and/or a grip.

As a second broad aspect of the invention, an electrosurgical apparatus is provided for treating tissue. The apparatus comprises: an elongate shaft having a proximal region, a distal region, which comprises a conductive region, and one or more lumens therethrough; one or more apertures defined by the shaft and in communication with at least one lumen; an occluding means occluding at least a portion of an opening defined by a distal end of the elongate shaft, where the occluding means is attached to the shaft through an attachment means, such as a weld joint, a solder joint and a mechanical crimp; a temperature sensing means associated with the distal region; a handle associated with the proximal region; an electrical connector flexibly coupled to the handle; and at least one fluid delivery interface connection flexibly coupled to the handle for coupling a fluid delivery mechanism to deliver a treatment composition to the tissue.

Another aspect of the invention provides a method for delivering energy to a treatment area of an animal body comprising the steps of: providing a treatment system comprising a power source, a fluid delivery mechanism and an electrosurgical apparatus; coupling the power source to the electrosurgical apparatus through an electrical coupling means; coupling the fluid delivery mechanism to the electrosurgical apparatus through a fluid delivery interface connection; positioning the apparatus at or in the vicinity of the treatment area; administering the treatment composition from the fluid delivery mechanism to the animal body via the electrosurgical apparatus while maintaining the position of the apparatus within the body; delivering energy from the power source to the body via the electrosurgical apparatus while maintaining the position of the apparatus within the body; and monitoring temperature at a distal region of the apparatus. The aforementioned procedure may be completed with the electrical coupling means and the fluid delivery interface connection remaining coupled to the apparatus.

BRIEF DESCRIPTION OF THE DRAWINGS

These and other features of the embodiments of the invention will become more apparent in the following detailed description in which reference is made to the appended drawings wherein.

DETAILED DESCRIPTION OF EMBODIMENTS

Figure 1:
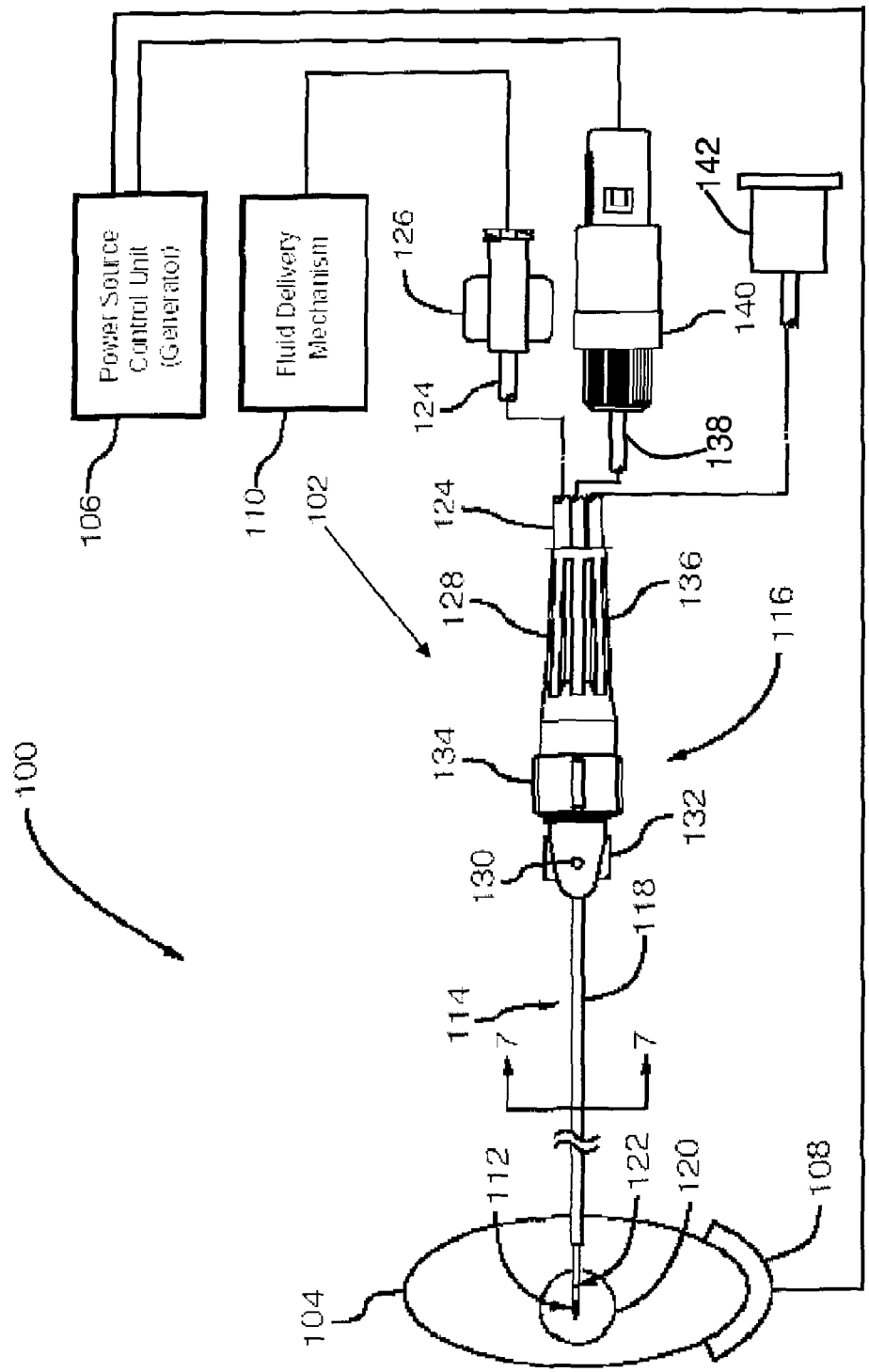
FIG. 1 is a plan elevation view, fragmented, of a system incorporating an electrosurgical apparatus in accordance with a first embodiment of the present invention.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. In some instances, well-known structures and/or processes may not have been described or shown in detail to not obscure the invention. Also, it is to be understood that the phraseology and terminology employed herein is for the purpose of description and should not be regarded as limiting. Further, it is contemplated that the term animals as used herein includes, but is not limited to, humans.

Referring first to FIG. 1, an apparatus 102 in accordance with a first embodiment of the surgical apparatus aspect of the invention is shown in a system 100 for treating a body 104. System 100 comprises the electrosurgical apparatus 102; a power source control unit 106; a return dispersive electrode 108; and a fluid delivery mechanism 110, such as, but not limited to, a syringe, for fluid composition injection. Power source control unit 106 may perform at least one of the following functions: supplying energy, for example RF energy, to apparatus 102; measuring temperature feedback from at least one temperature sensor of apparatus 102; and providing impedance measurement between a conductive region 112 of apparatus 102 and return dispersive electrode 108. Impedance measurement may be used during placement to target a body tissue that has specific electrical properties. Apparatus 102 may comprise a conductive shaft 114 and a handle 116. Conductive shaft 114 has an insulating coating 118 along a major portion of its outer surface, terminating adjacent exposed conductive region 112. Conductive region 112 may be operable to transmit energy to a target area 120 of body 104. In addition, conductive region 112 may aid in the penetration of apparatus 102 into body 104 and in the navigation of apparatus 102 to a desired target area 120. It will therefore be understood by a person skilled in the art that conductive region 112 can be of varying dimensions and shapes and may be positioned at various locations on an apparatus 102 of the present invention. For example, conductive region 112 can be pointed, sharp, blunt, or open, varying in shape in accordance with the requirements of different procedures. Also, while the length of conductive region 112 in the first embodiment is between about 2 mm to about 10 mm, this length may vary depending on procedural requirements. Conductive region 112 may optionally be made of medical grade stainless steel, but other conductive biocompatible materials may be used as well.

In the first embodiment, shaft 114 and conductive region 112 are made from a conductive material, for example, stainless steel. Insulating coating 118 can be made of any type of insulating material, including but not limited to Polyethylene Terepthalate (PET), to prevent shaft 114 from delivering high frequency electrical current to tissue surrounding shaft 114. This coating can be applied using dip coating, heat shrink coating or any other method that would be understood by a person skilled in the art.

Figure 2A:
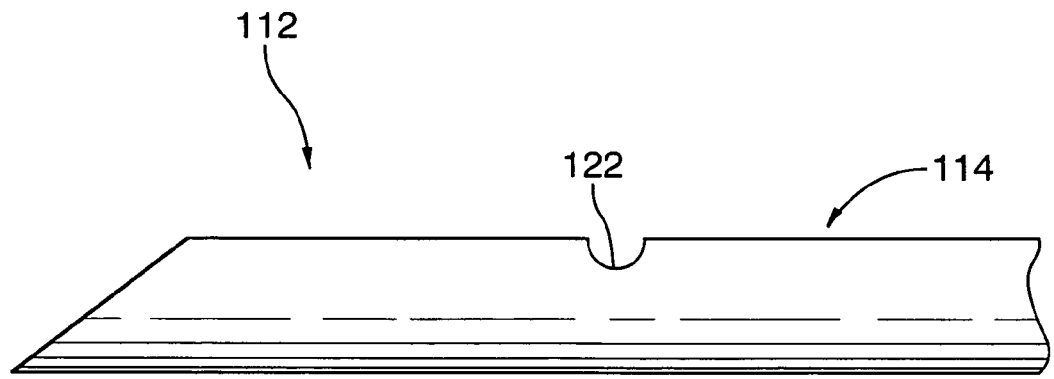
FIGS. 2A-2C are side elevation views of various embodiments of a distal region of an electrosurgical apparatus in accordance with the present invention.
Figure 2B:
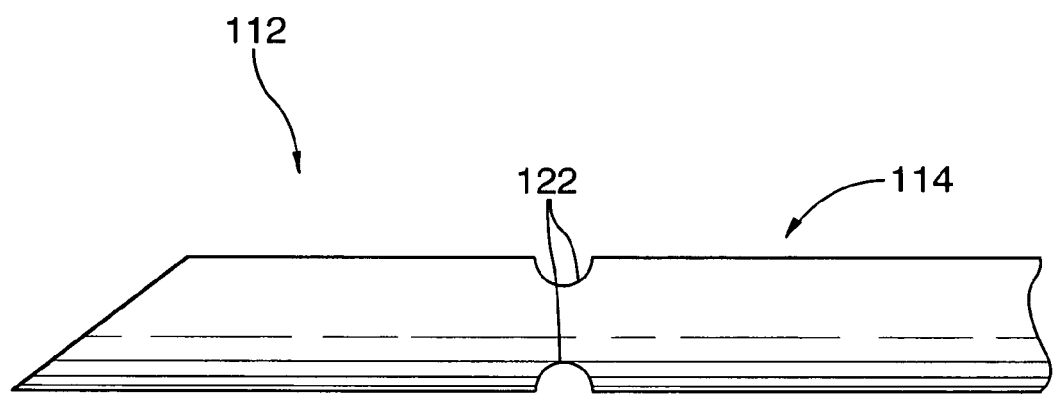
Figure 2C:
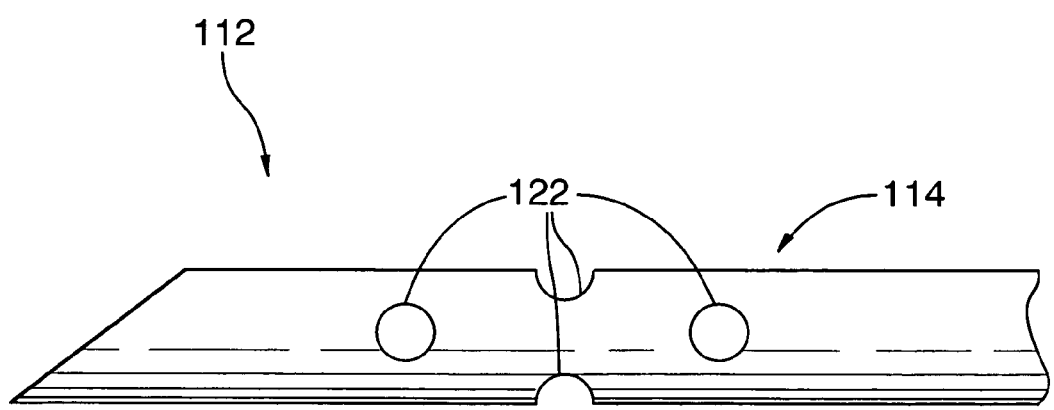

Shaft 114 optionally has at least one aperture 122, through which a treatment composition may exit from apparatus 102. In one embodiment, illustrated in FIG. 2A, aperture 122 is defined by conductive shaft 114 at a side thereof, for example at or proximate conductive region 112. The circumferential edge of aperture 122, on the outer wall of shaft 114, is optionally smooth to prevent cutting of tissue while apparatus 102 is inserted through body 104. In embodiments where aperture 122 is located at or proximate conductive region 112, aperture 122 beneficially allows fluid to be administered to body tissue 104 adjacent conductive region 112. If the treatment composition is electrically conductive, its delivery may provide better conductivity from conductive region 112 to target area 120 surrounding conductive region 112 and greater efficacy of the energy delivered to body tissue 104. A treatment composition may be delivered to a larger area of body tissue surrounding conductive region 112 by rotating apparatus 102 about the axis of conductive shaft 114 while simultaneously administering treatment composition through aperture 122. Furthermore, as shown in FIG. 2B, more than one aperture 122 may be disposed circumferentially around shaft 114 in order to allow for substantially simultaneous delivery of a treatment composition to a larger region of tissue surrounding conductive region 112. Alternatively or in addition, a treatment composition may be delivered to a specific region of tissue by rotating apparatus 102 about the axis of conductive shaft 114 to a desired orientation to target specific body tissue and subsequently administering treatment composition through aperture 122. In other embodiments, aperture 122 may be located at a different region of shaft 114, it may have various shapes and sizes and there may be more than one aperture 122. An exemplary depiction of such an embodiment is shown in FIG. 2C.

Conductive shaft 114 of apparatus 102 may impart rigidity to apparatus 102 to facilitate the maneuvering of conductive region 112 to reach target area 120, in which case shaft 114 may be referred to as being rigid or semi-rigid. In alternate embodiments, shaft 114 may be flexible. In the first embodiment of the invention, shaft 114 is hollow along its length, defining a lumen. Shaft 114 may be used to transmit a treatment composition to conductive region 112 and/or target area 120, as well as to support and enclose any wiring associated with apparatus 102. As well, an inner diameter of shaft 114 may be sufficiently dimensioned to accommodate a stylet or obturator in embodiments with an open tip, in addition to wiring for a temperature sensor associated with the distal end of shaft 114. In some embodiments, intended for use in spinal procedures, the length of shaft 114 may vary between about 5 cm to about 15 cm. It is understood, however, that the length may vary beyond this range according to the procedure being performed.

In the first embodiment, handle 116 optionally comprises a flexible tube 124 coupled thereto in fluid communication with the lumen of shaft 114. The flexibility of tube 124 may beneficially allow for greater maneuverability of apparatus 102. A proximal end of flexible tube 124 may be coupled to a fluid delivery interface connection 126. In other embodiments of the invention (not shown), handle 116 may not be necessary and flexible tube 124 may be coupled directly to shaft 114. Handle 116 also optionally provides a grip 128 to allow a user to manipulate apparatus 102. In one embodiment, handle 116 is manufactured from medical grade injection-moldable plastic or other material that can be sterilized using, for example, ethylene oxide. Handle 116 optionally has an aperture marker 130, in line with aperture 122 along the axis of shaft 114, to indicate the orientation of aperture 122 about the axis of shaft 114. Aperture marker 130 allows the user to target tissue for the delivery of a treatment composition by indicating the orientation of aperture 122. Handle 116 may further comprise orientation markings, including first orientation markings 132 to indicate, for example, 180° rotation of apparatus 102 about the axis of shaft 114 and second orientation markings 134 to indicate, for example, 90° rotation of apparatus 102 about the axis of shaft 114. The user may refer to first and/or second orientation markings 132,134 to prevent apparatus 102 from rotating about the axis of shaft 114 while apparatus 102 is inserted through body tissue 104, or to rotate apparatus 102 about the axis of shaft 114 to a desired orientation. First and second orientation markings 132, 134 may be visual indicators, which may be flush with handle 116, or tactile indicators, which may be textured or raised so that the user may see or feel markings 132, 134 as apparatus 102 is inserted into body 104. A proximal end of handle 116 optionally has a strain relief 136 with grip 128 running from the proximal end to the distal end of strain relief 136. In the depicted embodiment, grip 128 is textured, for example with parallel ridges, to provide points of friction for the user while apparatus 102 is rotated about the axis of shaft 114 and inserted through body 104. In this embodiment, the ridges on grip 128 may also be used to determine an angle of rotation of the apparatus. In one embodiment, strain relief 136 has a non-round (non-circular) cross-section, which may be square, triangular, or "toothed" like a mechanical gear. Strain relief 136 may be tapered with a larger distal outer diameter, in order to fit with handle 116, and a smaller proximal outer diameter, in order to secure electrical cable 138 and flexible tubing 124. This taper provides increased grip for the user and reduces slipping of the user's fingers as apparatus 102 is advanced into body 104. Strain relief 136 may provide a comfortable handle for the user and may conform to a user's gripping preference. Strain relief 136 may be, for example, a soft flexible bend relief able to support electrical cable 138 and flexible tubing 124. In the first embodiment shown in FIG. 1, electrical cable 138 and flexible tubing 124 extend from handle 116 and strain relief 136 in parallel and adjacent each other. Notably, in this embodiment, electrical cable 138 and flexible tubing 124 do not extend from handle 116 perpendicular to one another. This arrangement can provide a comfortable grasp and can enhance the ease of manipulation of apparatus 102 during placement, rotation, insertion, etc.

In the first embodiment, electrical energy may be supplied to conductive region 112 from power source control unit 106 via an electrical coupling, comprising electrical connector 140, electrical cable 138 and conductive shaft 114. All electrical contacts, except for conductive region 112, may be isolated from the user by a connector pin housing located in electrical connector 140. Electrical cable 138 may be flexible for flexibly coupling power source control unit 106 to conductive shaft 114, which supplies energy to conductive region 112. Electrical cable 138 may also relay temperature data back to power source control unit 106. In the first embodiment of the invention, one conductor in electrical cable 138 acts as both a thermocouple wire as well as an RF delivery wire, as will be described in greater detail below. Utilizing a single conductor for both purposes reduces the overall mass of electrical cable 138 and minimizes the forces and moments applied at handle 116 during placement of apparatus 102 in body tissue 104. It will be understood by a person skilled in the art that separate cables and/or conductors may alternatively be used in conjunction with a temperature sensor.

A fluid delivery mechanism 110 may be flexibly coupled to fluid delivery interface connection 126, and through it to shaft 114 via flexible tubing 124, in order to allow the administration of a treatment composition to a region of tissue in a patient's body. Therefore, as a benefit of the present invention, apparatus 102 may be simultaneously connected to fluid delivery mechanism 110 and power source control unit 106 in order to treat body 104. Fluid delivery interface connection 126 may be any connector including, but not limited to, a luer type connector, that allows for the flow of fluid from fluid delivery mechanism 110 to flexible tubing 124.

In operation of the first embodiment of the invention, apparatus 102 is inserted into body 104 and placed at target location 120. Proper placement of apparatus 102 may be confirmed by applying electrical energy, such as RF energy, using conductive region 112 to stimulate target area 120. An anesthetic fluid or another treatment composition can then be administered by actuating fluid delivery mechanism 110. Apart from pharmacological agents, including anesthetics, the applied treatment composition can include, for example, a fluid that is electrically conductive, a fluid used to heat or cool the tissue or a fluid, such as a dye, that may be used to help visualize a treatment site. The treatment composition exits fluid delivery mechanism 110 and flows through fluid delivery interface connection 126, flexible tube 124, and the lumen of shaft 114 to conductive region 112 where it exits through aperture 122. The incorporation of a fluid delivery system into apparatus 102, as herein described, beneficially allows fluid delivery mechanism 110 to be pre-connected to fluid delivery interface connection 126. Thus, the present invention helps to reduce the likelihood of inadvertent movement of conductive region 112 by removing the requirement to use and therefore remove a separate apparatus to apply a treatment composition, which would generally result in an adjustment of the position of conductive region 112. Additionally, the use of flexible tube 124 further decreases the forces acting on handle 116 and shaft 114 when fluid delivery mechanism 110 is actuated to administer the treatment composition, for example, when a plunger on a syringe is depressed. Therefore, after stimulation to confirm proper placement of apparatus 102, manual manipulation of apparatus 102 is minimized and thus the likelihood of shifting apparatus 102, and thus conductive region 112, out of position is decreased. In addition to, or in place of, electrical stimulation, other methods to confirm placement can also be used, such as measuring impedance or using imaging technologies, such as fluoroscopy. The use of an apparatus 102 with a shaft 114 whose distal end is sharp or pointed allows apparatus 102 to be inserted without the need to first insert a separate introducer tube or needle thus further reducing the likelihood of positional shifting of apparatus 102. However, the use of an introducer is also envisioned and is considered to be within the scope of the invention.

After optionally administering the treatment composition, a high frequency, for example RF, electrical current may be applied to target area 120 through conductive region 112. Return dispersive electrode 108 is provided to create a closed circuit when apparatus 102 is electrically operated in contact with body 104. Notably, since fluid delivery mechanism 110 is still connected to apparatus 102 during energy delivery, further delivery of treatment composition coincident with the delivery of energy is possible. During treatment, temperature sensor feedback may be used to automatically control the RF energy delivered to body tissue 104 to help ensure safe operation of apparatus 102. For example, if the body tissue temperature increases rapidly while applying RF energy as measured by the temperature sensor feedback mechanism, RF energy delivery to body tissue 104 may be suspended or reduced to provide a controlled ramp to the desired set temperature. In this manner, the user does not blindly apply RF energy to the body tissue, but is informed in real-time of the effects that RF energy delivery has on tissue temperature.

In some embodiments, as has been previously described, flexible tube 124 may provide the mechanical slack required to ensure that fluid delivery does not introduce added force to apparatus 102. Other treatment tools, depending on the procedure, may also be flexibly connected to apparatus 102. Apparatus 102 may therefore be provided with pre-formed connectors 142, as shown in FIG. 1, for these treatment tools that are flexibly coupled to apparatus 102.

In some embodiments of the invention, in order to facilitate precise placement of conductive region 112, conductive region 112 is made distinguishable from the rest of apparatus 102 when viewed under x-ray fluoroscopy (or other radiographic imaging modalities) by providing a radiopaque marking at or adjacent the proximal end of conductive region 112 or at another location of shaft 114. Alternatively, another form of marking, including, but not limited to, a magnetic or paramagnetic marking, may be provided, in order to visualize conductive region 112 using various medical imaging modalities such as MRI, ultrasound and CT.

Figure 3:
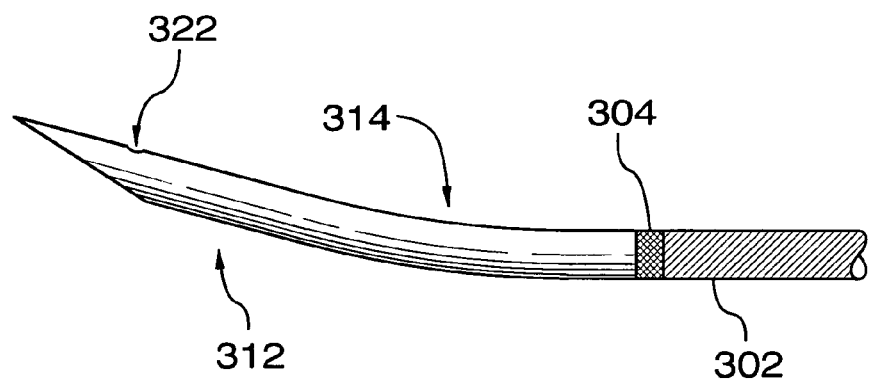
FIG. 3 is a side elevation view of a distal region of an electrosurgical apparatus in accordance with an alternate embodiment of the present invention.

Another embodiment of a shaft 114 of a surgical apparatus aspect of the invention can be seen in FIG. 3. This embodiment of shaft 114 comprises a textured surface 302, a radiopaque marker 304, and a curved conductive region 312. Conductive region 312 defines an aperture 322 on the inside of curve 314 and a temperature sensor (not shown) at or proximate the distal end of conductive region 312. Textured surface 302 allows for strong adhesion of insulating coating (not shown) to shaft 114 of apparatus 102 by increasing the shaft surface area. Radiopaque marker 304 provides visibility of the junction between curved conductive region 312 and insulated (or otherwise non-conductive) portions of shaft 114 under radiographic imaging. For example, radiopaque marker 304 may be placed so as to define the distal end point of the insulating coating (not shown) and the proximal start point of conductive region 312. It should be understood by those skilled in the art that radiopaque marker 304 may include any arrangement or length of radiopaque marking(s) along shaft 114 of apparatus 102. Other arrangements of radiopaque markings may include a series of equidistant markers to indicate insertion depth or may include radiopaque marking along the length of shaft 114, optionally proximal to conductive region 312. Equidistant depth markings may not necessarily be radiopaque, but may be colored to contrast with shaft 114 and to be visible to the user. Curved conductive region 312 provides added maneuverability of shaft 114 while it is advanced through body tissue 104. Having aperture 322 oriented on the inside of curve 314 prevents the edge of aperture 322 from cutting body tissue as shaft 114 is advanced through body tissue 104. However, aperture 322 may be positioned at various locations of shaft 114 and the invention is not limited in this regard. Furthermore, it should be noted that alternate embodiments of the present invention may comprise an apparatus having a curve without a textured surface or a textured surface without a curve. In addition, a curve may be present at other locations of shaft 114. Further embodiments of the present invention may comprise a shape altering mechanism (or a shape actuator) in order to steer apparatus 102 within a patient's body. The shape actuator may include, but is not limited to, cables for a mechanical actuator, hydraulic or piezo-electric devices and solenoids.

Figure 4A:
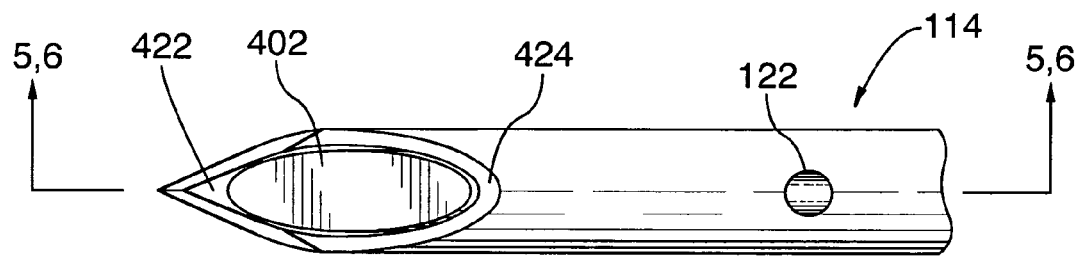
FIGS. 4A-4B are plan elevation views of a distal region of an electrosurgical apparatus in accordance with two embodiments of the present invention comprising a stylet.
Figure 4B:
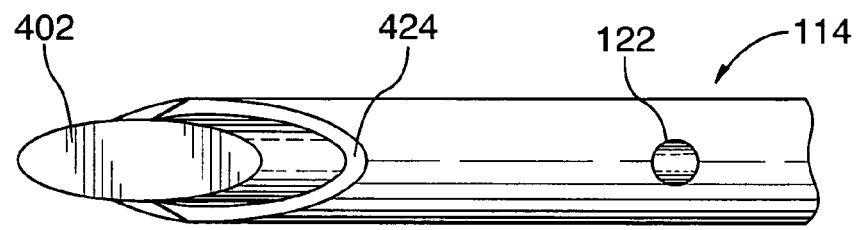
Figure 5A:
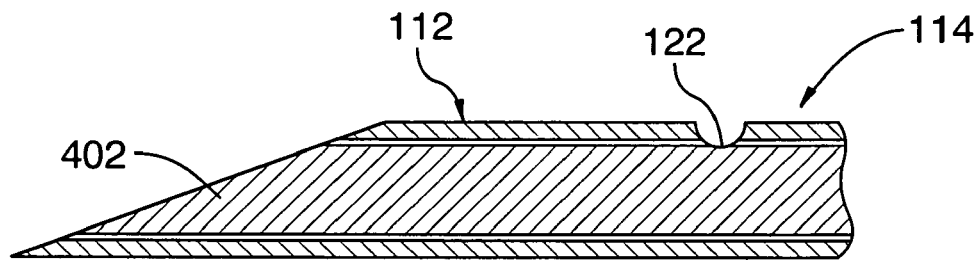
FIGS. 5A-5C are sectional side views through the shaft of various embodiments of the present invention comprising a stylet.
Figure 5B:
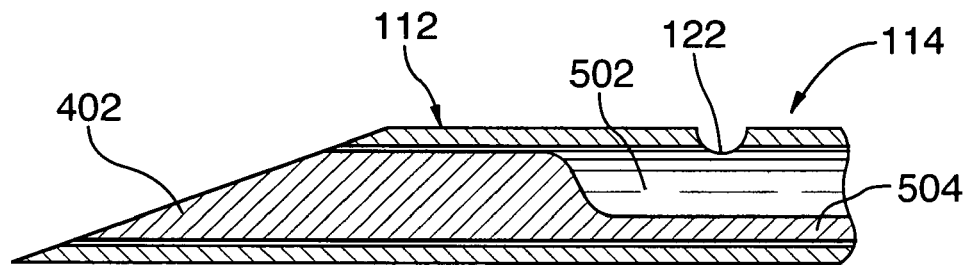
Figure 5C:
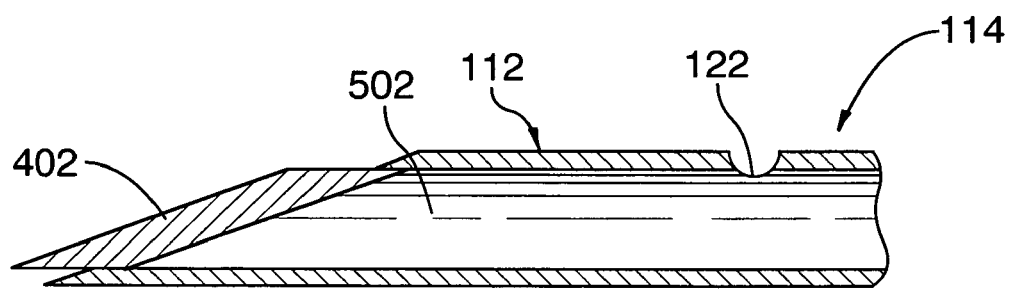

As has been described with respect to the first embodiment of the present invention, shaft 114 may be sufficiently dimensioned so as to accommodate a stylet or obturating device. Enlarged top elevation views of two exemplary embodiments of the distal region of apparatus 102, comprising a stylet 402, are shown in FIG. 4. Referring first to FIG. 4A, shaft 114 defines a distal aperture 422 at a distal end 424 thereof and the lumen of shaft 114 contains stylet 402, substantially occluding distal aperture 422 of shaft 114; in such an embodiment, a distal end of stylet 402 has substantially the same shape as that of distal end 424 of shaft 114 and is flush with distal end 424. Stylet 402 serves to discourage tissue from entering the lumen of shaft 114. FIG. 4B shows an alternate embodiment whereby stylet 402 protrudes from the distal end 424 of shaft 114. In further embodiments, only a portion of stylet 402 may protrude from distal end 424 of shaft 114. Alternatively, stylet 402 may not completely occlude distal aperture 422. For example, at least a portion of stylet 402 may be recessed inwards from the distal end 424 of shaft 114. FIG. 5 shows various embodiments of the disposition of stylet 402 within shaft 114. In one embodiment, shown in FIG. 5A, stylet 402 may substantially fill the lumen defined by shaft 114. Alternatively, stylet 402 may only partially fill the lumen, leaving a luminal space 502 between the exterior surface of a stylet shaft 504 and the interior surface of shaft 114, as shown in FIG. 5B. Although FIG. 5B shows stylet shaft 504 extending along one side of shaft 114, it should be understood that stylet shaft 504 can be located at any position within shaft 114, for example near the center of shaft 114. In a further embodiment, shown in FIG. 5C, stylet 402 is in the form of a cap or plug that occludes at least a portion of distal end 424 of shaft 114 and that may be affixed to the distal end of shaft 114, for example by welding, but which does not extend through the length of shaft 114.

Stylet 402 may be removable from shaft 114, or may be affixed to shaft 114, for example by welding, at one or more locations. Where stylet 402 is positioned such that a luminal space 502 is present, welding stylet 402 to shaft 114 can serve to reduce the radial and axial movement of stylet 402 within shaft 114.

In one specific embodiment, stylet 402 may be made from a conductive material, such as stainless steel. In this embodiment, stylet 402 may be connected to shaft 114 or may be otherwise electrically coupled to shaft 114 and may thus be operable to deliver energy to a patient's body. Alternatively, stylet 402 may be independently connected to power source control unit 106. If stylet 402 is conductive and is coupled to shaft 114 or power source control unit 106, conductive region 112 may be defined as comprising the portions of shaft 114 and stylet 402 that deliver energy to target tissue area 120.

Figure 6A:
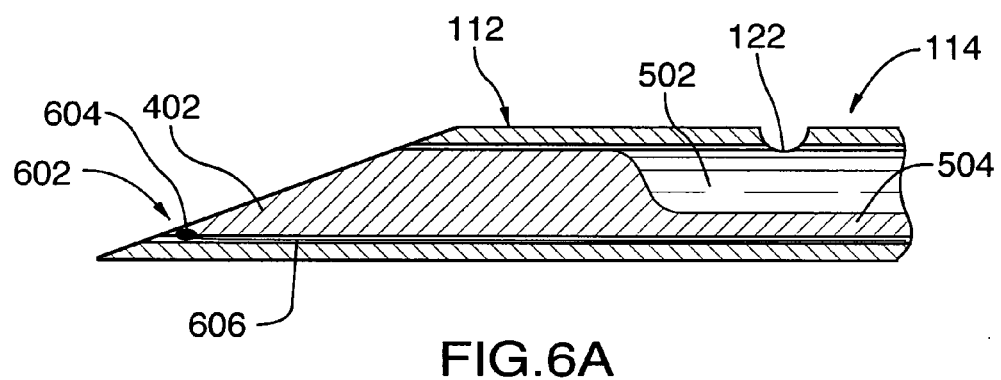
FIGS. 6A-6B are sectional side views through the shaft of two exemplary embodiments of the present invention, comprising a stylet and a thermocouple.
Figure 6B:
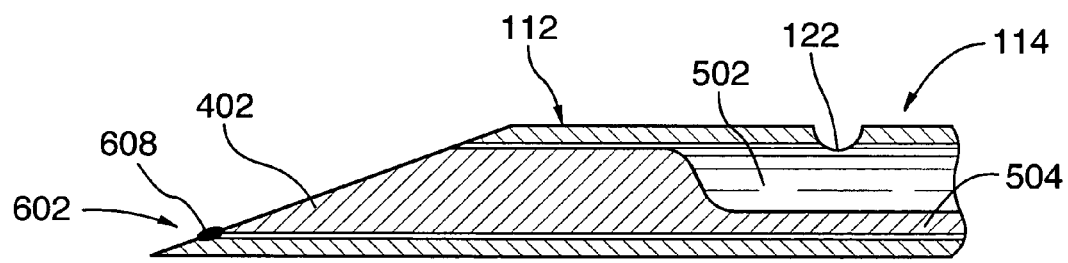

FIG. 6 shows two exemplary embodiments of a distal region of apparatus 102 comprising a temperature sensor 602, aperture 122 and conductive region 112 (including the conductive regions of shaft 114 and stylet 402 where applicable, as described above). Temperature sensor 602 may be welded to the distal end of conductive region 112, for example, either to shaft 114 or to stylet 402. In some embodiments, as has been mentioned, temperature sensor 602 is a thermocouple, which may optionally include one or more thermocouple wires running in the lumen of shaft 114 and insulated from conductive shaft 114 and from any other conductive structure electrically coupled to shaft 114 or to power source control unit 106. Insulation may include either insulation on the luminal surface (the surface facing the lumen through which the wire or wires run) of shaft 114 and other conductive structures, or insulation on the outer wall of the wire or wires.

The general use of a thermocouple to measure temperature is known in the art. However, in one embodiment, conductive region 112 may be a component of thermocouple 602, as follows: the distal end of a thermocouple wire, made of a material that differs from the material of conductive region 112, may be minimally stripped of insulation; temperature sensor 602 may then be formed by welding the distal end of the thermocouple wire to conductive region 112 of shaft 114 to create a thermocouple. Thus, shaft 114 and conductive region 112 may serve dual purposes, being utilized for energy delivery as well as forming a portion of temperature sensor 602. In other embodiments, rather than forming a temperature sensor using conductive region 112, as described above, a separate, self-contained temperature sensor may be attached to conductive region 112. In any embodiment of the present invention, temperature sensor 602 need not comprise a thermocouple, and may comprise a thermistor, thermometer, optical temperature sensor or other temperature sensor. Furthermore, apparatus 102 may contain any number of temperature sensors, which may be positioned at a variety of locations along the side of the apparatus, not only at or near conductive region 112, and which may protrude from, be flush with, or be recessed into the surface of conductive shaft 114. In embodiments comprising a stylet 402 and a thermocouple 602, stylet 402 may be a component of thermocouple 602. In one such embodiment, illustrated in FIG. 6A, thermocouple junction 604 is formed by the welding of a wire 606 to stylet 402. For example, if stylet 402 was made from stainless steel, a constantan (or any other wire made of a conductive material other than stainless steel) wire 606 might be used. In such an embodiment, stylet 402 may be welded or otherwise connected to shaft 114 at some other location of shaft 114. In another embodiment, shown in FIG. 6B, stylet 402 may be made of one metal (for example, constantan) and shaft 114 may be made of a dissimilar metal (for example, stainless steel); stylet 402 may then be welded to shaft 114 in order to create a thermocouple junction 608. In such an embodiment, a constantan wire (not shown) may extend from a proximal end of stylet shaft 504 in order to provide temperature information to power source control unit 106. Although thermocouple junction 608 is shown at a tip of shaft 114, other embodiments may have thermocouple junction 608 at an alternate location along shaft 114. As has already been mentioned, more than one temperature sensor may be present on apparatus 102 and any temperature sensor may be a thermocouple, thermistor or other temperature sensing means.

In the first embodiment, the distal end of shaft 114 is sharpened in order to allow apparatus 102 to be inserted into body 104 without the use of an introducer tube or needle. Alternatively, in another embodiment, shaft 114 may not be sharpened, but stylet 402 may be sharpened or pointed and may protrude from shaft 114 in order achieve the same results as when shaft 114 is itself sharpened. As noted earlier, the circumferential edge of aperture 122, on the outer surface of shaft 114, is optionally smooth to prevent cutting of body tissue 104 while apparatus 102 is advanced therethrough. In some embodiments, stylet 402 may not completely occlude shaft 114, allowing treatment composition to exit a distal end of shaft 114 if it is in communication with fluid delivery mechanism 110. Thus, the term "aperture" as used herein is meant to include any opening in the body of shaft 114 and is not limited to a lateral aperture 122.

While the term stylet is used to refer to structure 402 as shown in the various figures, this term is not intended to be exclusive, and is meant to include any obturator, trocar or other structure which, in embodiments with an open distal end, at least partially obstructs the distal end of shaft 114, in order to, for example, prevent the passage of tissue into shaft 114. The incorporation of a stylet into an apparatus of the present invention may be beneficial in that it may facilitate the incorporation of a temperature sensor 602 into apparatus 102 and make the process of manufacturing apparatus 102 more efficient.

Figure 7A:
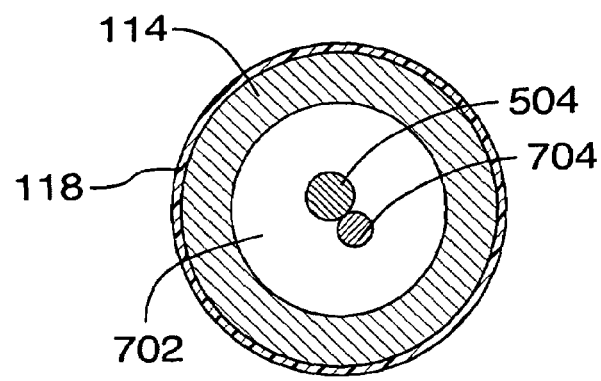
FIGS. 7A-7C are sectional front views through the shafts of various embodiments of an electrosurgical apparatus in accordance with the present invention.
Figure 7B:
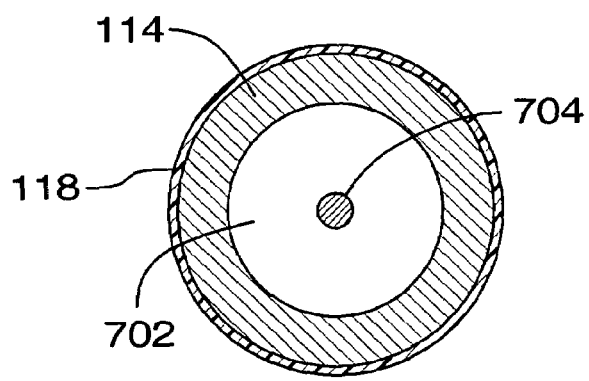
Figure 7C:
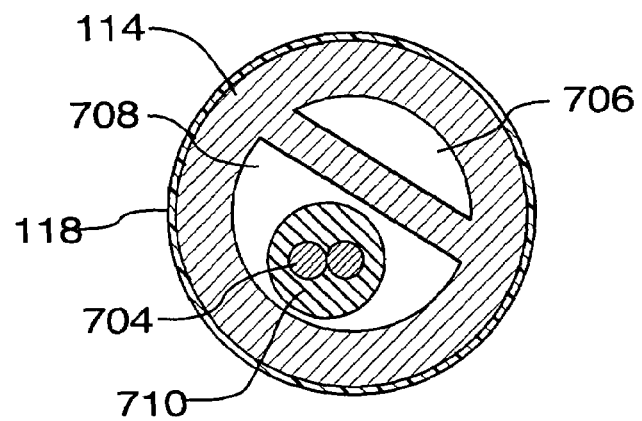

Referring now to FIG. 7, sectional side views of a portion of conductive shaft 114 comprising insulating coating 118, as illustrated in FIG. 1, are shown. In the embodiment shown in FIG. 7A, shaft 114 defines a lumen 702, as has been described. Stylet shaft 504 and temperature measurement wire or wires 704 run through lumen 702. In one embodiment, the present invention comprises a single wire 704 housed in lumen 702 of conductive shaft 114, and welded to a dissimilar metal to form temperature sensor 602. As mentioned above, the welding of wire 704 to a dissimilar metal may entail welding to shaft 114 or to stylet 402. Alternatively, temperature wires 704 may comprise two or more wire components of a temperature sensor associated with apparatus 102. Although FIGS. 7A and 7B show wire 704 and stylet shaft 504 (in FIG. 7A; in the embodiment shown in FIG. 7B, stylet shaft 504 is not present within lumen 702) located substantially in the center of lumen 702 defined by shaft 114, it should be clear that this is not intended to be limiting and that wire or wires 704 and/or stylet shaft 504 may be located at various positions within lumen 702. Another embodiment of a shaft 114 of apparatus 102 is shown in FIG. 7C. This embodiment comprises a first lumen 706 and a second lumen 708. Wiring 704 for temperature sensor 602 and conductive region 112 (in embodiments comprising such wiring) of apparatus 102 run through second lumen 708, optionally contained within an insulating covering 710. First lumen 706 may be beneficially used as a passage for the injection of a treatment composition. The size of lumen 706 and lumen 708 and the number of lumens required may vary depending on the embodiment. Another embodiment (not shown) comprises a plurality of lumens, for example as shown in FIG. 7C, as well as a stylet housed within one of the lumens.

Figure 8:
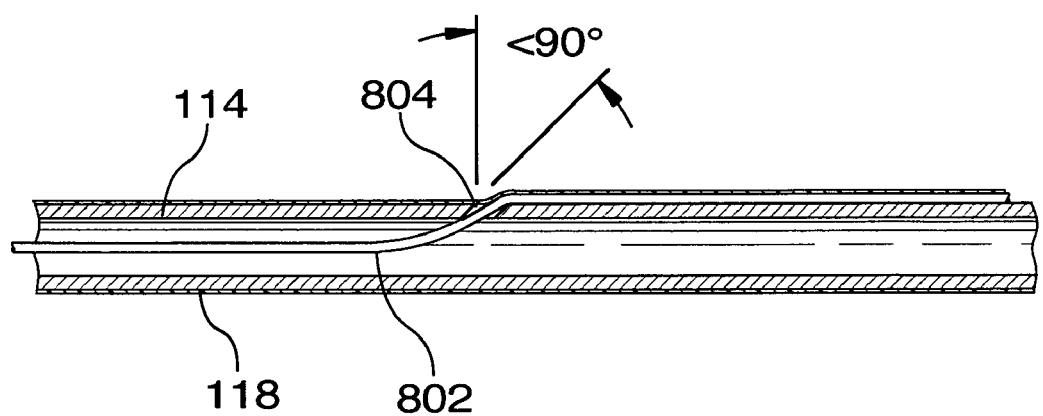
FIG. 8 is a sectional side view through the shaft of one embodiment of an electrosurgical apparatus in accordance with the present invention.

Referring now to FIG. 8, a magnified sectional view of a portion of shaft 114, according to one embodiment of the present invention, is shown. In this embodiment, thermocouple wiring 802 exits the lumen of conductive shaft 114 through a wiring aperture 804. Wiring aperture 804 is optionally angled less than 90° with respect to the axis of conductive shaft 114, as shown in FIG. 8, in order to minimize bending of wiring 802. Use of this angle provides additional strain relief and protects the insulation of thermocouple wiring 802 as it exits shaft 114, lies parallel to conductive shaft 114, and is covered by insulating coating 118. In alternate embodiments, any wires may exit shaft 114 at any angle. In yet further embodiments, all wires associated with apparatus 102 may remain within shaft 114 until a proximal end of shaft 114 is reached.

Figure 9A:
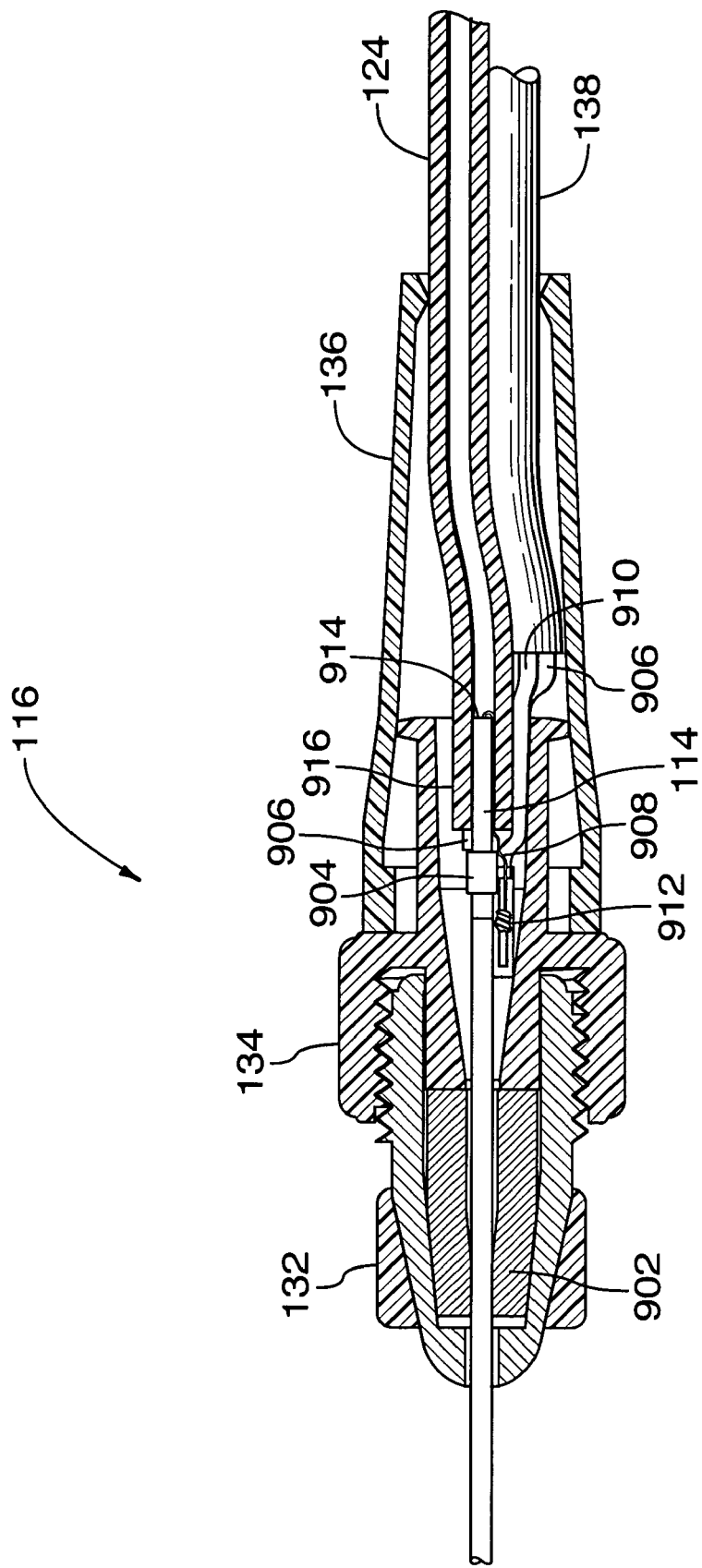
FIGS. 9A-9B are sectional top views through two embodiments of the handle of an electrosurgical apparatus in accordance with the present invention.

FIG. 9 shows two magnified sectional top views (taken from a horizontal plane through apparatus 102) of exemplary embodiments of handle 116. Referring initially to the first embodiment, as depicted in FIG. 9A, handle 116 further comprises a compression gasket 902 to provide radial centering of shaft 114 in handle 116. A crimp joint 904 provides electrical coupling between a first conductor 906 of electrical cable 138 and conductive shaft 114. As described with reference to FIG. 1, first conductor 906 may beneficially be used both as a thermocouple wire as well as an RF delivery wire, as was mentioned with respect to the possible dual functionality of shaft 114 and conductive region 112. In the embodiment shown, a second thermocouple wire 908 may be electrically coupled to a second conductor 910 of electrical cable 138 at solder joint 912, and may enter conductive shaft 114 at a proximal end 914 of shaft 114. Although elements 904 and 912 have been described as crimp and solder joints, respectively, other means of electrical coupling are envisioned for either element as well, including but not limited to soldering, mechanical crimping and welding. Flexible tube 124 is coupled to conductive shaft 114 at junction 916 and is slid over proximal end 914. Junction 916 thus helps to provide fluid communication from fluid delivery mechanism 110 to aperture 122.

Figure 9B:
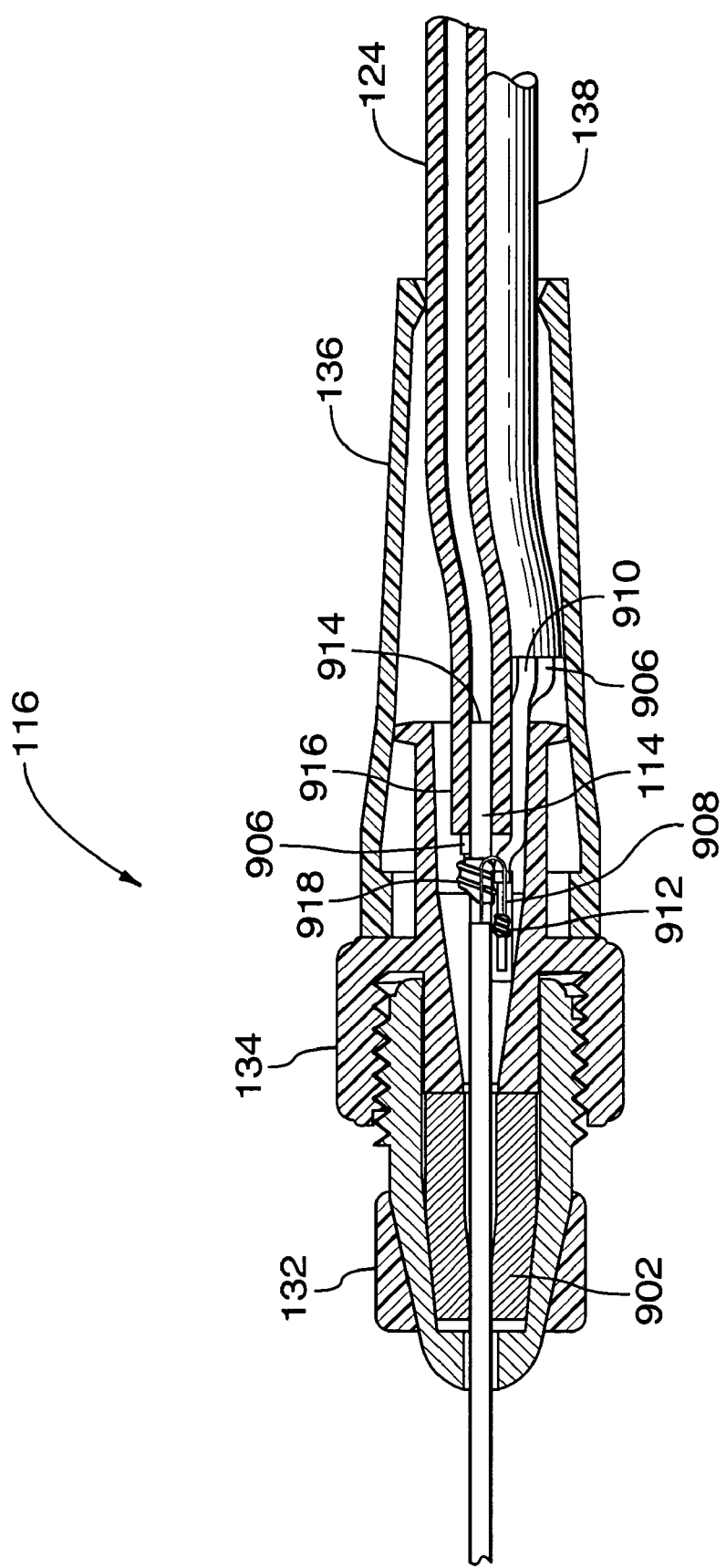

In the embodiment shown in FIG. 9B, a solder joint 918 provides electrical coupling between a first conductor 906 of electrical cable 138 and conductive shaft 114. In the embodiment shown, a second thermocouple wire 908 may be electrically coupled to a second conductor 910 of electrical cable 138 at solder joint 912 and may run along shaft 114 beneath insulating coating 118. Although elements 918 and 912 have been described as solder joints, other means of electrical coupling are envisioned as well, including but not limited to mechanical crimping and welding.

Figure 10:
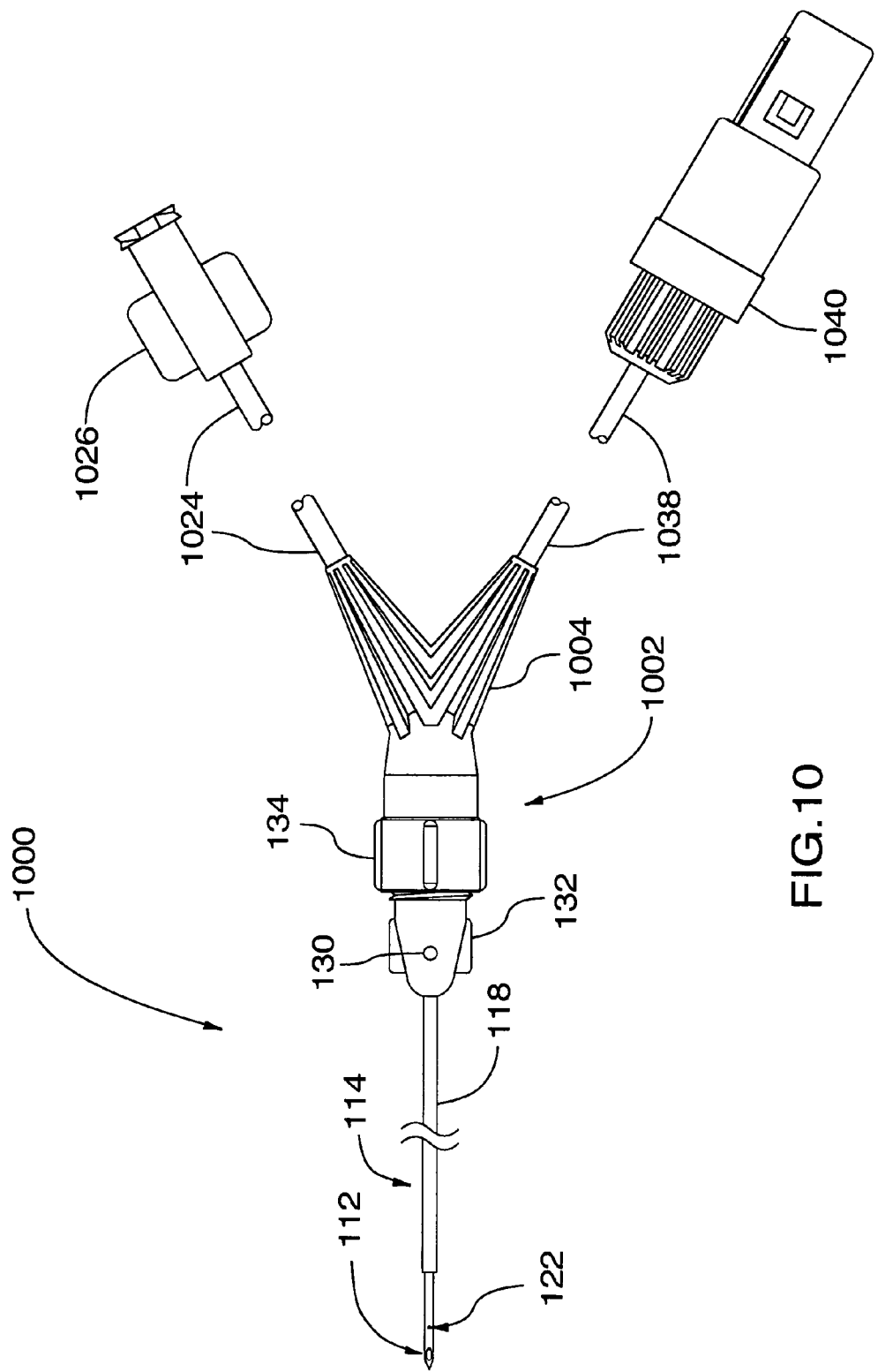
FIG. 10 is a plan elevation view of an electrosurgical apparatus having a V-shaped handle in accordance with an alternate embodiment of the invention.

Another embodiment of an apparatus aspect of the present invention is shown in FIG. 10. An apparatus 1000 has a handle 1002 configured to reduce torque. Handle 1002 incorporates a "V" shaped housing section 1004 having one arm for coupling to a treatment composition tube 1024 and a second arm for coupling to an electrical cable 1038. Treatment composition tube 1024 and electrical cable 1038 extend from the end of handle 1002 and are coupled to fluid delivery interface connection 1026 and electrical connector 1040, respectively, to substantially reduce the force transmitted to a conductive region 112. Similar to apparatus 102, apparatus 1000 in FIG. 10 may also comprise a temperature sensor (not shown), an insulating coating 118, an aperture 122, first orientation markings 132 to indicate, for example, 180° rotation, second orientation markings 134 to indicate, for example, 90° rotation, and an aperture marker 130 to indicate a location of aperture 122. It will be understood that the extent to which tube 1024 extends into handle 1002 or onto shaft 1024 can vary so long as it is in fluid communication with an aperture 122.

Though not shown, another embodiment of a surgical apparatus aspect of this invention provides an apparatus comprising a shaft 114 and a conductive region 112 constructed from separate components. Shaft 114 could be made of a conductive material and then coated with an insulating material as in the embodiment shown in FIG. 1 or could be made from a non-conductive material such as, but not restricted to, polyetheretherketone (PEEK). Conductive region 112 is made of a conductive material and attached to non-conductive shaft 114. There are various methods in which conductive region 112 could be attached to non-conductive shaft 114 including, but not limited to, chemical bonding, press fits and screw fits. The wiring for temperature sensor 602 (in embodiments comprising a temperature sensor) and the conductive region (i.e. the wire or other means of transmitting electrical energy from a power source to the conductive region) may extend through and along a lumen of shaft 114 and connect to conductive region 112. Alternately, in any of the embodiments of the present invention, the wiring for one or more of temperature sensor 602 and conductive region 112 may be extruded in the walls of shaft 114 such that the lumen could be used to deliver treatment composition but may not be required to house wiring.

Conductive region 112 can therefore serve multiple purposes. Conductive region 112 can be the site of passage for electric current to the surrounding tissue. It can also be the site for the release of a treatment composition. Finally, conductive region 112 can also house one or more temperature sensors 602. Various tip geometries, such as a bevel on the end of the conductive region with a bottom hole and a mid-bevel temperature sensor are also contemplated embodiments (not shown). It should be understood that various other tip shapes and sizes; aperture sizes and placements, and temperature sensor placements are also considered to be viable options for this invention.

Figure 11A:
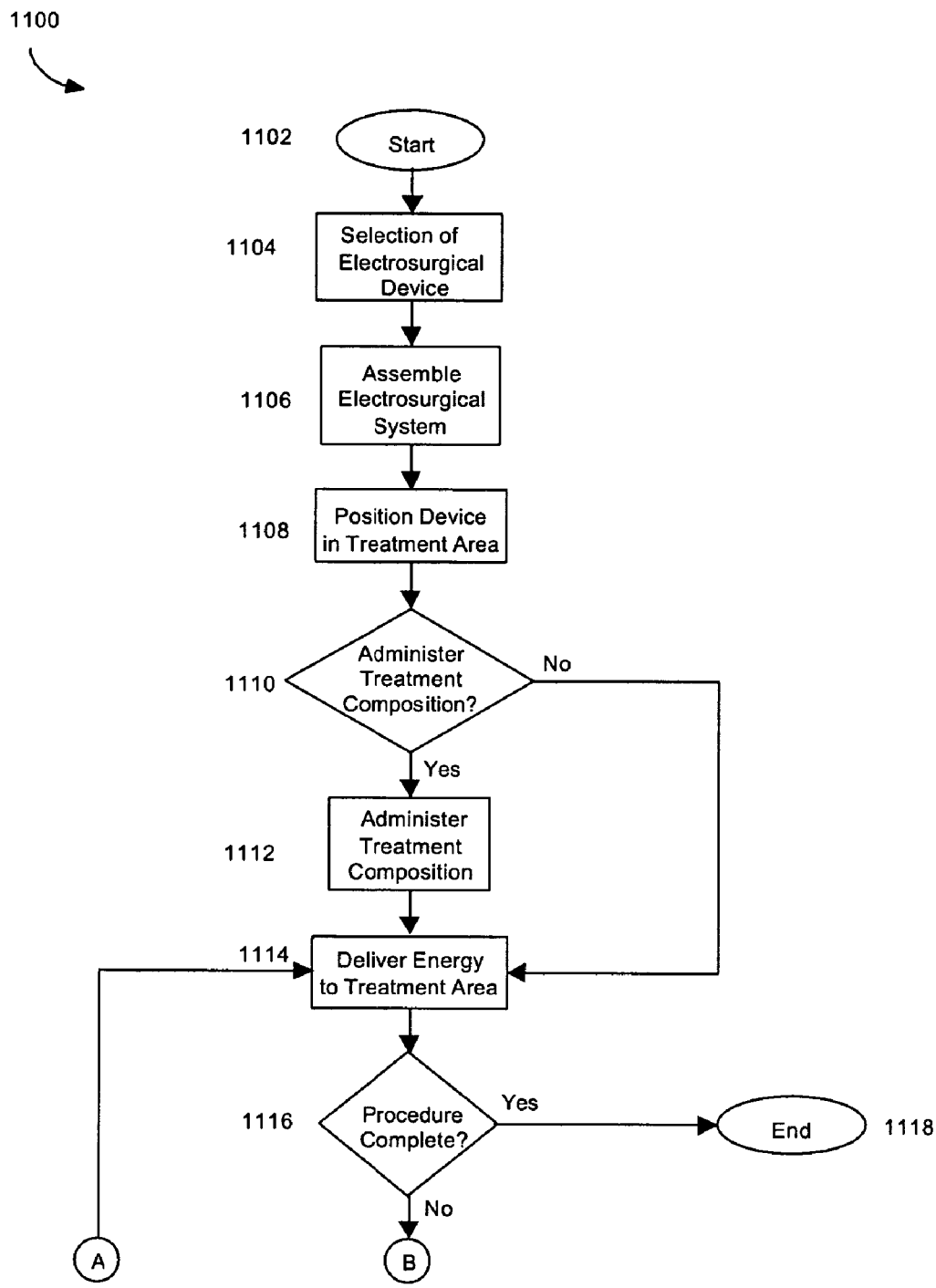
FIGS. 11A-11B are first and second partial flowcharts of operations according to one embodiment of a method aspect of the present invention.
Figure 11B:
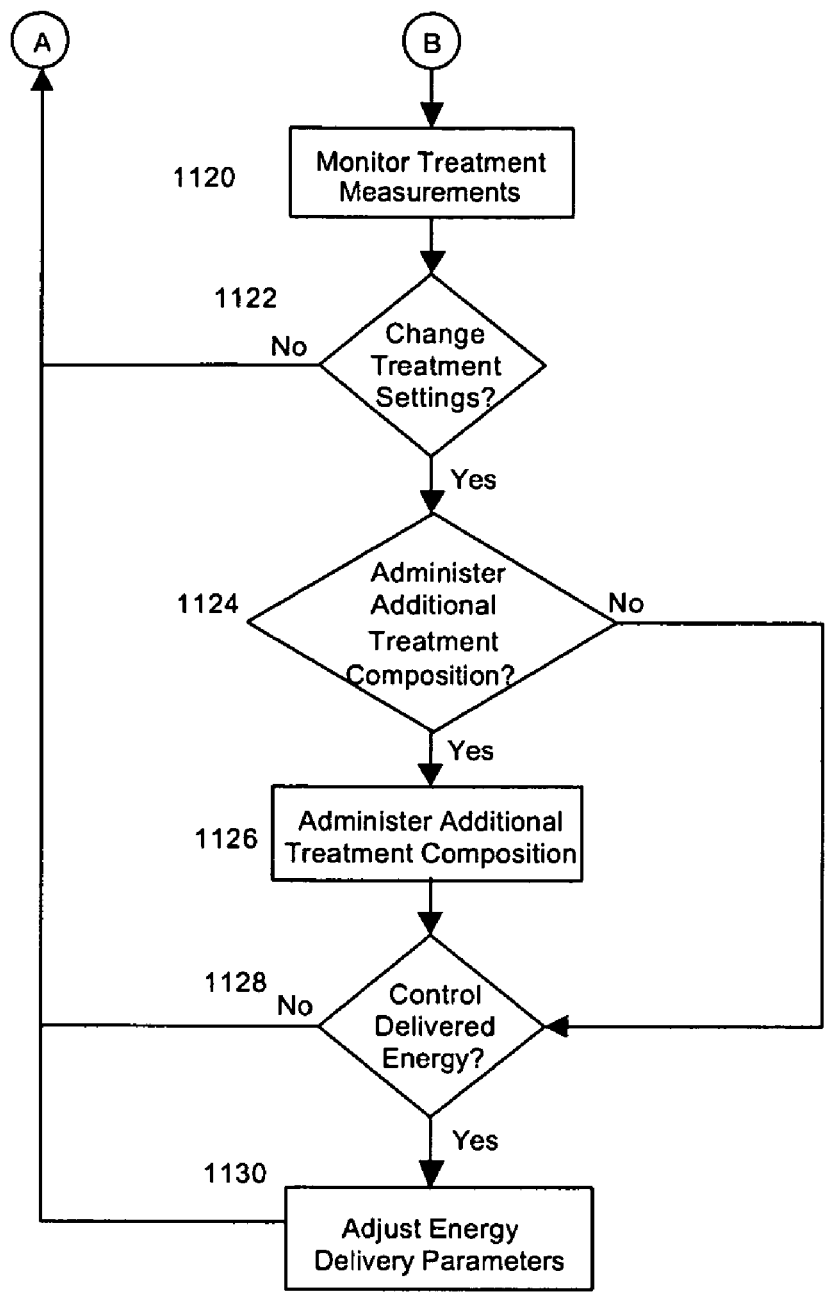

Referring to FIGS. 11A and 11B, a flowchart of operations 1100, in accordance with one embodiment of a method aspect of the invention, is illustrated. At step 1102, the method for using electrosurgical apparatus 102 is initiated. At step 1104, an electrosurgical apparatus in accordance with the apparatus aspect of the present invention, is selected and obtained for performing the electrosurgical procedure. Reference to electrosurgical apparatus 102 of FIG. 1 in connection with the method aspect of the invention is intended to be exemplary and illustrative only. Selection may thus include choosing one of an assortment of electrosurgical devices or apparatuses for appropriate dimension, such as length, tip shape, active tip length, gauge, etc. Selection may also include obtaining an electrosurgical device or apparatus from many devices or apparatuses and removing the one electrosurgical device or apparatus from packaging materials. At step 1106, an electrosurgical system, such as system 100 in FIG. 1, is assembled. Assembly may include attachment of fluid delivery mechanism 110 and/or attachment of power source control unit 106, as shown in FIG. 1. Assembly may also include the placement of return dispersive electrode 108 on body 104. The order in which fluid delivery mechanism 110, power source control unit 106 and return dispersive electrode 108, are assembled, may vary with user preference. Partial assembly of electrosurgical system 100 is also possible; for example, the user may wish to place return dispersive electrode 108 and power source control unit 106, but leave fluid delivery mechanism 110 detached from the system until a later step. Although a first embodiment of the method includes the attachment of power source control unit 106, fluid delivery mechanism 110, and return dispersive electrode 108, it will be understood by those skilled in the art that variations in order of attachment may occur.

At step 1108, the electrosurgical apparatus is positioned in body 104. The step of positioning the electrosurgical apparatus may comprise a step of percutaneous insertion of the distal end of apparatus 102 into body 104. The step of positioning may further comprise a step of utilizing an aid to precisely position the apparatus. For example, a visual, tactile or radiopaque marker may be used to help determine a location of the apparatus within body 104. Visualization may involve the use of fluoroscopic, x-ray or other imaging. In addition, a user may monitor impedance of tissue as apparatus 102 is inserted through body 104 in order to position the apparatus within a desired tissue region. Alternatively, a user may deliver stimulation energy to body 104 in order to ascertain the proximity of apparatus 102 to various neural structures, thus facilitating the placement of apparatus 102 at a desired location within body 104. In a first embodiment of a method aspect of the present invention, apparatus 102 is inserted to a final placement position in target area 120 of body 104. However, positioning of apparatus 102 at any initial placement location may be performed at step 1108 and positioning of apparatus 102 in a final location may occur later, but before delivering energy at step 1114.

At step 1110, the user decides whether or not to administer a treatment composition to body 104. The decision to administer treatment composition may include factors such as the preference of the physician, allergic reactions to treatment composition, and/or the delivery of nerve stimulation energy rather than nerve ablation energy. In the preferred embodiment, the user decides to administer treatment composition fluid and treatment composition fluid is administered via Yes branch to step 1112. Administration of treatment composition fluid may include, but is not limited to, injection of sterile water or saline solution to modify electrical properties of a body tissue, injection of local anesthetic solution to block, hinder or change the signal propagation of pain from the body tissue and injection of a dye for visualization of the body tissue. It will be understood by those skilled in the art that other treatment fluids or combinations of the abovementioned treatment fluids may be injected into the body tissue surrounding a distal region of apparatus 102. In step 1110, if the user decides to not administer treatment composition fluid, the user chooses to deliver energy to the treatment area via No branch to step 1114. Although this first embodiment of the method invention comprises the administration of treatment composition fluid at step 1112 prior to delivery of energy to treatment area at step 1114, administration of treatment composition fluid may rather occur during and/or after delivery of energy to treatment area or may not occur at all.

While energy is being delivered to treatment area 120 at step 1114, the user and/or power source control unit 106 monitors for completion of energy delivery to treatment area 120 at step 1116. This monitoring may include, but is not limited to, user comparison of elapsed time while energy is being delivered to body tissue compared to the desired or set time for which delivery of energy to treatment area should occur, user choice to terminate energy delivery, logic in power source control unit 106 to end energy delivery upon detection of a system error during energy delivery, and/or measurement in power source control unit 106 to automatically terminate energy delivery upon elapsed time reaching desired treatment time, which is set on power source control unit 106. System errors may include, but are not limited to, detection of discontinuity between electrosurgical apparatus 102 and power source control unit 106, high or low impedance between conductive region 112 and return dispersive electrode 108 and delivered power exceeding power limit. Alternatively, energy delivery may be altered depending on feedback from temperature and/or impedance measurements, as described with respect to step 1120 below. If it is determined that energy delivery to the treatment area should be terminated, the procedure is stopped at step 1118 via the Yes branch. If energy delivery to the treatment area is not complete in step 1116, measurements from electrosurgical apparatus 102 at treatment area 120 are monitored manually by the user or automatically by power source control unit 106 at step 1120 (FIG. 8B) via No branch from step 1116.

In the first embodiment, temperature measurement of treatment area 120 is monitored at step 1120. Monitoring of temperature in treatment area 120 may include, but is not limited to, the measurement of temperature through the use of a temperature sensor, such as a thermocouple or thermistor, feedback to power source control unit 106, and temperature data display on a display or monitor, which may be separate from power source control unit 106. In the first embodiment of the method invention, temperature of tissue in the treatment area is fed back to power source control unit 106 to be used for decision-making at step 1122. At step 1122, the measured temperature (or other measurement) of treatment area 120 is compared against predetermined values. These values may include value ranges, threshold values, individual values, etc. The user, who is continuously monitoring the temperature (or other measurement) of treatment area 120, may make the comparison of measured temperature (or other measurement) against acceptable/unacceptable values. Alternatively, in the first embodiment, power source control unit 106 automatically compares the measured temperature (or other measurement) to predetermined values and makes a decision whether the measured temperature is acceptable or unacceptable. Notably at step 1120, power source control unit 106 or the user may also monitor other measurements related to treatment area such as impedance, power, current and voltage, and use these measurements to make one or more decisions at step 1122. If the measured temperature (and/or other measured parameters) is acceptable, energy delivery settings are not changed and energy delivery to treatment area continues via No branch back to step 1114. If the measured temperature is unacceptable, treatment settings may be changed via Yes branch to step 1124. At step 1124, the user has the option to administer additional treatment composition fluid via fluid delivery mechanism 110. This additional treatment composition may include, but is not limited to, any of the treatment compositions mentioned with respect to step 1112. Administration of additional treatment composition fluid may occur at any time before, during, or after energy is being delivered to treatment area. Step 1124 may also be the initial delivery of treatment composition to treatment area if the user had decided to not administer treatment composition at step 1110. If the user decides to administer treatment composition at step 1124, additional treatment composition is administered to treatment area via Yes branch to step 1126. With the completion of step 1126, or if the user decides not to administer treatment composition at step 1124, the user and/or power source control unit 106 has the option to modify system 100 settings to control energy being delivered to treatment area at step 1128.

The option to modify system 100 settings, at step 1128, may include, but is not limited to, a user choice to manually change power setting to increase/decrease temperature of treatment area 120, a user choice to increase/decrease set temperature of system to change lesion size, and an automatic change in power setting to control temperature of treatment area 120. At step 1128, if the user and/or power source control unit 106 decide(s) not to modify system 100 settings to control energy being delivered, energy continues to be delivered to treatment area 120 via No branch at step 1114. If the user decides to manually modify or change the system 100 settings to control energy being delivered to treatment area 120, system settings are manually adjusted via Yes branch to step 1130. Alternatively and in the first embodiment, if the power source control unit provides automatic control of energy delivery to treatment area and power source control unit 106 determines that system 100 parameter settings must be adjusted, adjustment occurs automatically via Yes branch to step 1130. Automatic control may include the ability of power source control unit 106 to continuously monitor treatment measurements, compare said measurements to acceptable values, ranges, etc., make decisions based on said comparison and modify system parameter settings to obtain acceptable treatment measurements. System parameter settings may include, but are not limited to, settings for power, current, voltage, temperature, delivery rates and treatment time. Treatment measurements may include, but are not limited to, measurement of impedance, voltage, current, power, temperature, continuity between electrosurgical apparatus 102 and power source control unit and error checking. After all required adjustments are made, either manually by the user or automatically by power source control unit 106, energy continues to be delivered to treatment area 120, using the new settings, at step 1114. The treatment procedure beneficially continues from step 1114 through to step 1130 until step 1118 is reached.

The embodiments of the invention described above are intended to be exemplary only. For example, although the invention has been described primarily utilizing RF or other high-frequency energy, other forms of energy may be used as well, including but not limited to thermal energy. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An electrosurgical apparatus for treating tissue comprising:
   an elongate shaft having a proximal region, a distal region comprising a conductive region and one or more lumens therethrough;
   one or more apertures defined by the shaft in communication with at least one of said one or more lumens;
   a stylet occluding at least a portion of an opening defined by a distal end of said elongate shaft;
   an electrical connector permanently coupled to said proximal region via a flexible electrical cable for coupling said shaft to a power source for supplying energy to said conductive region;
   a temperature sensor associated with said distal region; and
   at least one fluid delivery interface connection permanently coupled to said proximal region via a flexible tube for coupling a fluid delivery mechanism to deliver a treatment composition through at least one of said one or more apertures;
   wherein said temperature sensor comprises a thermocouple and wherein said stylet is a component of said thermocouple.

2. The electrosurgical apparatus of claim 1, wherein said stylet is attached to said shaft.

3. The electrosurgical apparatus of claim 2, wherein said stylet is attached to said shaft through an attachment means selected from the group consisting of a weld joint, a solder joint and a mechanical crimp.

4. The electrosurgical apparatus of claim 1, wherein said portion of an opening comprises a majority of an opening defined by said distal end of said shaft and wherein a distal end of said stylet is flush with said distal end of said elongate shaft.

5. The electrosurgical apparatus of claim 1, further comprising at least one connector flexibly coupled at or near said proximal region for coupling at least one treatment tool.

6. The electrosurgical apparatus of claim 1, wherein at least one of said one or more apertures is located in a side of said shaft.

7. The electrosurgical apparatus of claim 6, wherein said at least one of said one or more apertures has a smooth edge for minimizing trauma to bodily tissue.

8. The electrosurgical apparatus of claim 6, further comprising a marker associated with said proximal region to indicate an orientation of said at least one of said one or more apertures.

9. The electrosurgical apparatus of claim 1, wherein at least one of said one or more apertures is associated with said distal region of said shaft.

10. The electrosurgical apparatus of claim 9, wherein said at least one of said one or more apertures is defined by a space between said stylet and said shaft.

11. The electrosurgical apparatus of claim 1, wherein said distal end of said shaft comprises a shape that facilitates penetration of tissue.

12. The electrosurgical apparatus of claim 1, wherein at least one of said one or more lumens houses wiring.

13. The electrosurgical apparatus of claim 12, wherein said wiring couples said conductive region to said power source.

14. The electrosurgical apparatus of claim 12, wherein at least a portion of said wiring is connected to said temperature sensor.

15. The electrosurgical apparatus of claim 1, further comprising a handle associated with said proximal region, wherein said handle is coupled to said elongate shaft.

16. The electrosurgical apparatus of claim 15, wherein said handle comprises at least one marking to indicate rotation of the apparatus about a longitudinal axis of said elongate shaft.

17. The electrosurgical apparatus of claim 16, wherein said handle comprises two or more markings and wherein at least two markings are located on opposing faces of said handle.

18. The electrosurgical apparatus of claim 15, wherein said handle further comprises a strain relief supporting at least one of said electrical cable, said tube and wiring extending from said handle.

19. The electrosurgical apparatus of claim 18, wherein said strain relief holds at least two of said electrical cable, said tube and wiring closely together and parallel to a longitudinal axis of said handle.

20. The electrosurgical apparatus of claim 15, wherein said handle further comprises a grip to ease handling of the apparatus during insertion and rotation.

21. The electrosurgical apparatus of claim 20, wherein said grip comprises a means of determining an orientation of said apparatus.

22. The electrosurgical apparatus of claim 1, further comprising a radiopaque marker.

23. The electrosurgical apparatus of claim 15, wherein said electrical cable and said flexible tubing extend from said handle closely together and parallel to a longitudinal axis of said handle.

24. A treatment procedure for delivering energy to a treatment area of an animal body comprising:
- providing a treatment system comprising a power source, a fluid delivery mechanism and an electrosurgical apparatus;
- coupling said power source to said electrosurgical apparatus at a distance from said electrosurgical apparatus through an electrical coupling means flexibly coupled to said electrosurgical apparatus while maintaining said position of said apparatus within said animal body;
- coupling said fluid delivery mechanism to said electrosurgical apparatus at a distance from said electrosurgical apparatus through a fluid delivery interface connection coupled to said electrosurgical apparatus via a flexible tube while maintaining said position of said apparatus within said animal body;
- positioning the apparatus at or in the vicinity of a treatment area within said animal body;
- administering a treatment composition from said fluid delivery mechanism to said animal body via said electrosurgical apparatus while maintaining the position of the apparatus within said animal body;
- delivering energy from said power source to said animal body via said electrosurgical apparatus; and
- monitoring temperature at a distal region of said electrosurgical apparatus;
- wherein coupling said energy source and said fluid delivery mechanism to said electrosurgical apparatus at a distance from the electrosurgical apparatus reduces forces on the electrosurgical apparatus and allows said position of said electrosurgical apparatus to be maintained during the course of said treatment procedure.

25. An electrosurgical apparatus for treating tissue comprising:
- an elongate shaft having a proximal region, a distal region comprising a conductive region and one or more lumens therethrough;
- one or more apertures defined by the shaft in communication with at least one of said one or more lumens;
- a stylet occluding at least a portion of an opening defined by a distal end of said elongate shaft;
- an electrical connector permanently coupled to said proximal region via a flexible electrical cable for coupling said shaft to a power source for supplying energy to said conductive region;
- a temperature sensor associated with said distal region; and
- at least one fluid delivery interface connection permanently coupled to said proximal region via a flexible tube for coupling a fluid delivery mechanism to deliver a treatment composition through at least one of said one or more apertures;
- wherein said temperature sensor comprises a thermocouple and wherein said conductive region is a component of said thermocouple.

* * * * *